United States Patent [19]

Baeck et al.

[11] Patent Number: 5,520,838
[45] Date of Patent: May 28, 1996

US005520838A

[54] COMPACT DETERGENT COMPOSITIONS WITH HIGH ACTIVITY CELLULASE

[75] Inventors: Andre C. Baeck, Bonheiden; Raphael A. Ceulemans, Lubbeek; Alfred Busch, Londerzeel, all of Belgium

[73] Assignee: The Procter & Gamble Company, Cincinnati, Ohio

[21] Appl. No.: 81,328

[22] PCT Filed: Jan. 15, 1992

[86] PCT No.: PCT/US92/00203

§ 371 Date: Nov. 19, 1993

§ 102(e) Date: Nov. 19, 1993

[87] PCT Pub. No.: WO91/05841

PCT Pub. Date: Feb. 5, 1991

[30] Foreign Application Priority Data

Jan. 16, 1991 [EP] European Pat. Off. .............. 91870006
Nov. 6, 1991 [EP] European Pat. Off. .............. 91202879

[51] Int. Cl.[6] .................................................. C11D 3/386
[52] U.S. Cl. ........................... 252/174.12; 252/DIG. 12; 252/173; 252/90; 435/209; 435/183; 435/264
[58] Field of Search ................... 252/174.12, DIG. 12, 252/173, 90; 435/209, 183, 264

[56] References Cited

U.S. PATENT DOCUMENTS

| 4,435,307 | 3/1984 | Barbesgaard | 252/174.12 |
|---|---|---|---|
| 4,738,682 | 4/1988 | Boegh et al. | 8/401 |
| 4,822,516 | 4/1989 | Suzuki et al. | 252/174.12 |
| 4,978,470 | 12/1990 | Suzuki et al. | 252/174.12 |
| 4,999,138 | 3/1991 | Nebashi | 252/543 |

FOREIGN PATENT DOCUMENTS

| 0220016 | 4/1987 | European Pat. Off. . |
|---|---|---|
| 0269169 | 6/1988 | European Pat. Off. . |
| 0350098 | 1/1990 | European Pat. Off. . |
| 0367339 | 5/1990 | European Pat. Off. . |
| 0381397 | 8/1990 | European Pat. Off. . |
| 63-69894 | 3/1988 | Japan . |
| WO8904862 | 6/1989 | WIPO . |
| 8909259 | 10/1989 | WIPO . |
| WO9105841 | 5/1991 | WIPO . |
| 9117243 | 11/1991 | WIPO . |

*Primary Examiner*—Linda Skaling Therkorn
*Assistant Examiner*—Kerry A. Fries
*Attorney, Agent, or Firm*—F. A. Borrego; T. D. Reed; K. W. Zerby

[57] ABSTRACT

The present invention concerns cellulase-containing granular detergent compositions which are in a "compact" form, i.e. they are of a relatively high density and contain a relatively low amount of inorganic filler salt compared to conventional detergent compositions. In the detergent compositions herein the cellulase is defined by the C14CMC method described herein and preferably comprises a specific single-component endoglucanase.

21 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 1060 base pairs
( B ) TYPE: nucleic acid
( C ) STRANDEDNESS: unknown
( D ) TOPOLOGY: unknown ( i x ) FEATURE:
( A ) NAME/KEY: CDS
( B ) LOCATION: 10..924

( x i ) SEQUENCE DESCRIPTION: SEQ ID NO:1:

```
GGATCCAAG ATG CGT TCC TCC CCC CTC CTC CCG TCC GCC GTT GTG GCC        48
          Met Arg Ser Ser Pro Leu Leu Pro Ser Ala Val Val Ala
          -21 -20              -15                 -10

GCC CTG CCG GTG TTG GCC CTT GCC GCT GAT GGC AGG TCC ACC CGC TAC       96
Ala Leu Pro Val Leu Ala Leu Ala Ala Asp Gly Arg Ser Thr Arg Tyr
            -5                   1                 5

TGG GAC TGC TGC AAG CCT TCG TGC GGC TGG GCC AAG AAG GCT CCC GTG      144
Trp Asp Cys Cys Lys Pro Ser Cys Gly Trp Ala Lys Lys Ala Pro Val
        10              15                  20

AAC CAG CCT GTC TTT TCC TGC AAC GCC AAC TTC CAG CGT ATC ACG GAC      192
Asn Gln Pro Val Phe Ser Cys Asn Ala Asn Phe Gln Arg Ile Thr Asp
25                  30                  35                  40

TTC GAC GCC AAG TCC GGC TGC GAG CCG GGT GTC GCC TAC TCG TGC          240
Phe Asp Ala Lys Ser Gly Cys Glu Pro Gly Val Ala Tyr Ser Cys
                45                  50                  55

GCC GAC CAG ACC CCA TGG GCT GTG AAC GAC GAC TTC GCG CTC GGT TTT      288
Ala Asp Gln Thr Pro Trp Ala Val Asn Asp Asp Phe Ala Leu Gly Phe
            60                  65                  70

GCT GCC ACC TCT ATT GCC GGC AGC AAT GAG GCG GGC TGG TGC TGC GCC      336
Ala Ala Thr Ser Ile Ala Gly Ser Asn Glu Ala Gly Trp Cys Cys Ala
        75                  80                  85

TGC TAC GAG CTC ACC TTC ACA TCC GGT CCT GTT GCT GGC AAG AAG ATG      384
Cys Tyr Glu Leu Thr Phe Thr Ser Gly Pro Val Ala Gly Lys Lys Met
    90                  95                  100

GTC GTC CAG TCC ACC AGC ACT GGC GGT GAT CTT GGC AGC AAC CAC TTC      432
Val Val Gln Ser Thr Ser Thr Gly Gly Asp Leu Gly Ser Asn His Phe
105             110                 115                 120

GAT CTC AAC ATC CCC GGC GGC GGC GTC GGC ATC TTC GAC GGA TGC ACT      480
Asp Leu Asn Ile Pro Gly Gly Gly Val Gly Ile Phe Asp Gly Cys Thr
                125                 130                 135

CCC CAG TTC GGC GGT CTG CCC GGC CAG CGC TAC GGC GGC ATC TCG TCC      528
Pro Gln Phe Gly Gly Leu Pro Gly Gln Arg Tyr Gly Gly Ile Ser Ser
            140                 145                 150

CGC AAC GAG TGC GAT CGG TTC CCC GAC GCC CTC AAG CCC GGC TGC TAC      576
Arg Asn Glu Cys Asp Arg Phe Pro Asp Ala Leu Lys Pro Gly Cys Tyr
        155                 160                 165

TGG CGC TTC GAC TGG TTC AAG AAC GCC GAC AAT CCG AGC TTC AGC TTC      624
Trp Arg Phe Asp Trp Phe Lys Asn Ala Asp Asn Pro Ser Phe Ser Phe
    170                 175                 180

CGT CAG GTC CAG TGC CCA GCC GAG CTC GTC GCT CGC ACC GGA TGC CGC      672
Arg Gln Val Gln Cys Pro Ala Glu Leu Val Ala Arg Thr Gly Cys Arg
185                 190                 195                 200

CGC AAC GAC GAC GGC AAC TTC CCT GCC GTC CAG ATC CCC TCC AGC AGC      720
Arg Asn Asp Asp Gly Asn Phe Pro Ala Val Gln Ile Pro Ser Ser Ser
                205                 210                 215

ACC AGC TCT CCG GTC AAC CAG CCT ACC AGC ACC AGC ACC ACG TCC ACC      768
Thr Ser Ser Pro Val Asn Gln Pro Thr Ser Thr Ser Thr Thr Ser Thr
            220                 225                 230

TCC ACC ACC TCG AGC CCG CCA GTC CAG CCT ACG ACT CCC AGC GGC TGC      816
Ser Thr Thr Ser Ser Pro Pro Val Gln Pro Thr Thr Pro Ser Gly Cys
        235                 240                 245

ACT GCT GAG AGG TGG GCT CAG TGC GGC GGC AAT GGC TGG AGC GGC TGC      864
Thr Ala Glu Arg Trp Ala Gln Cys Gly Gly Asn Gly Trp Ser Gly Cys
    250                 255                 260

ACC ACC TGC GTC GCT GGC AGC ACT TGC ACG AAG ATT AAT GAC TGG TAC      912
Thr Thr Cys Val Ala Gly Ser Thr Cys Thr Lys Ile Asn Asp Trp Tyr
265                 270                 275                 280

CAT CAG TGC CTG TAGACGCAGG GCAGCTGAG GGCCTTACTG GTGGCCGCAA           964
His Gln Cys Leu
```

```
His Gln Cys Leu
          285
```

CGAAATGACA CTCCCAATCA CTGTATTAGT TCTTGTACAT AATTTCGTCA TCCCTCCAGG    1024

GATTGTCACA TAAATGCAAT GAGGAACAAT GAGTAC    1060

( 2 ) INFORMATION FOR SEQ ID NO:2:

( i ) SEQUENCE CHARACTERISTICS:
        ( A ) LENGTH: 305 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Arg Ser Ser Pro Leu Leu Pro Ser Ala Val Val Ala Ala Leu Pro
-21 -20              -15                 -10

Val Leu Ala Leu Ala Ala Asp Gly Arg Ser Thr Arg Tyr Trp Asp Cys
 -5               1               5                   10

Cys Lys Pro Ser Cys Gly Trp Ala Lys Lys Ala Pro Val Asn Gln Pro
             15              20              25

Val Phe Ser Cys Asn Ala Asn Phe Gln Arg Ile Thr Asp Phe Asp Ala
         30              35                  40

Lys Ser Gly Cys Glu Pro Gly Gly Val Ala Tyr Ser Cys Ala Asp Gln
     45              50                  55

Thr Pro Trp Ala Val Asn Asp Asp Phe Ala Leu Gly Phe Ala Ala Thr
 60              65              70                      75

Ser Ile Ala Gly Ser Asn Glu Ala Gly Trp Cys Cys Ala Cys Tyr Glu
             80              85                      90

Leu Thr Phe Thr Ser Gly Pro Val Ala Gly Lys Lys Met Val Val Gln
             95              100             105

Ser Thr Ser Thr Gly Gly Asp Leu Gly Ser Asn His Phe Asp Leu Asn
         110             115             120

Ile Pro Gly Gly Gly Val Gly Ile Phe Asp Gly Cys Thr Pro Gln Phe
    125             130             135

Gly Gly Leu Pro Gly Gln Arg Tyr Gly Gly Ile Ser Ser Arg Asn Glu
140             145             150                     155

Cys Asp Arg Phe Pro Asp Ala Leu Lys Pro Gly Cys Tyr Trp Arg Phe
             160             165             170

Asp Trp Phe Lys Asn Ala Asp Asn Pro Ser Phe Ser Phe Arg Gln Val
             175             180             185

Gln Cys Pro Ala Glu Leu Val Ala Arg Thr Gly Cys Arg Arg Asn Asp
             190             195             200

Asp Gly Asn Phe Pro Ala Val Gln Ile Pro Ser Ser Ser Thr Ser Ser
    205             210             215

Pro Val Asn Gln Pro Thr Ser Thr Ser Thr Thr Ser Thr Ser Thr Thr
220             225             230                     235

Ser Ser Pro Pro Val Gln Pro Thr Thr Pro Ser Gly Cys Thr Ala Glu
             240             245             250

Arg Trp Ala Gln Cys Gly Gly Asn Gly Trp Ser Gly Cys Thr Thr Cys
             255             260             265

Val Ala Gly Ser Thr Cys Thr Lys Ile Asn Asp Trp Tyr His Gln Cys
             270             275             280

Leu
```

( 2 ) INFORMATION FOR SEQ ID NO:3:

(i) SEQUENCE CHARACTERISTICS:
  (A) LENGTH: 1473 base pairs
  (B) TYPE: nucleic acid
  (C) STRANDEDNESS: unknown
  (D) TOPOLOGY: unknown (ix) FEATURE:
  (A) NAME/KEY: CDS
  (B) LOCATION: 97..1224

(xi) SEQUENCE DESCRIPTION: SEQ ID NO:3:

```
GAATTCGCGG CCGCTCATTC ACTTCATTCA TTCTTTAGAA TTACATACAC TCTCTTTCAA        60

AACAGTCACT CTTTAAACAA AACAACTTTT GCAACA ATG CGA TCT TAC ACT CTT        114
                                        Met Arg Ser Tyr Thr Leu
                                         1                     5

CTC GCC CTG GCC GGC CCT CTC GCC GTG AGT GCT GCT TCT GGA AGC GGT        162
Leu Ala Leu Ala Gly Pro Leu Ala Val Ser Ala Ala Ser Gly Ser Gly
             10                  15                  20

CAC TCT ACT CGA TAC TGG GAT TGC TGC AAG CCT TCT TGC TCT TGG AGC        210
His Ser Thr Arg Tyr Trp Asp Cys Cys Lys Pro Ser Cys Ser Trp Ser
         25                  30                  35

GGA AAG GCT GCT GTC AAC GCC CCT GCT TTA ACT TGT GAT AAG AAC GAC        258
Gly Lys Ala Ala Val Asn Ala Pro Ala Leu Thr Cys Asp Lys Asn Asp
     40                  45                  50

AAC CCC ATT TCC AAC ACC AAT GCT GTC AAC GGT TGT GAG GGT GGT GGT        306
Asn Pro Ile Ser Asn Thr Asn Ala Val Asn Gly Cys Glu Gly Gly Gly
 55                  60                  65                  70

TCT GCT TAT GCT TGC ACC AAC TAC TCT CCC TGG GCT GTC AAC GAT GAG        354
Ser Ala Tyr Ala Cys Thr Asn Tyr Ser Pro Trp Ala Val Asn Asp Glu
                 75                  80                  85

CTT GCC TAC GGT TTC GCT GCT ACC AAG ATC TCC GGT GGC TCC GAG GCC        402
Leu Ala Tyr Gly Phe Ala Ala Thr Lys Ile Ser Gly Gly Ser Glu Ala
             90                  95                 100

AGC TGG TGC TGT GCT TGC TAT GCT TTG ACC TTC ACC ACT GGC CCC GTC        450
Ser Trp Cys Cys Ala Cys Tyr Ala Leu Thr Phe Thr Thr Gly Pro Val
        105                 110                 115

AAG GGC AAG AAG ATG ATC GTC CAG TCC ACC AAC ACT GGA GGT GAT CTC        498
Lys Gly Lys Lys Met Ile Val Gln Ser Thr Asn Thr Gly Gly Asp Leu
    120                 125                 130

GGC GAC AAC CAC TTC GAT CTC ATG ATG CCC GGC GGT GGT GTC GGT ATC        546
Gly Asp Asn His Phe Asp Leu Met Met Pro Gly Gly Gly Val Gly Ile
135                 140                 145                 150

TTC GAC GGC TGC ACC TCT GAG TTC GGC AAG GCT CTC GGC GGT GCC CAG        594
Phe Asp Gly Cys Thr Ser Glu Phe Gly Lys Ala Leu Gly Gly Ala Gln
                155                 160                 165

TAC GGC GGT ATC TCC TCC CGA AGC GAA TGT GAT AGC TAC CCC GAG CTT        642
Tyr Gly Gly Ile Ser Ser Arg Ser Glu Cys Asp Ser Tyr Pro Glu Leu
            170                 175                 180

CTC AAG GAC GGT TGC CAC TGG CGA TTC GAC TGG TTC GAG AAC GCC GAC        690
Leu Lys Asp Gly Cys His Trp Arg Phe Asp Trp Phe Glu Asn Ala Asp
        185                 190                 195

AAC CCT GAC TTC ACC TTT GAG CAG GTT CAG TGC CCC AAG GCT CTC CTC        738
Asn Pro Asp Phe Thr Phe Glu Gln Val Gln Cys Pro Lys Ala Leu Leu
    200                 205                 210

GAC ATC AGT GGA TGC AAG CGT GAT GAC GAC TCC AGC TTC CCT GCC TTC        786
Asp Ile Ser Gly Cys Lys Arg Asp Asp Asp Ser Ser Phe Pro Ala Phe
215                 220                 225                 230

AAG GTT GAT ACC TCG GCC AGC AAG CCC CAG CCC TCC AGC TCC GCT AAG        834
Lys Val Asp Thr Ser Ala Ser Lys Pro Gln Pro Ser Ser Ser Ala Lys
                235                 240                 245
```

| | | | | | | | | | | | | | | | |
|---|---|---|---|---|---|---|---|---|---|---|---|---|---|---|---|
| AAG | ACC | ACC | TCC | GCT | GCT | GCT | GCC | GCT | CAG | CCC | CAG | AAG | ACC | AAG | GAT |
| Lys | Thr | Thr | Ser | Ala | Ala | Ala | Ala | Ala | Gln | Pro | Gln | Lys | Thr | Lys | Asp |
| | | | 250 | | | | | 255 | | | | | 260 | | |

882

| | | | | | | | | | | | | | | | |
|---|---|---|---|---|---|---|---|---|---|---|---|---|---|---|---|
| TCC | GCT | CCT | GTT | GTC | CAG | AAG | TCC | TCC | ACC | AAG | CCT | GCC | GCT | CAG | CCC |
| Ser | Ala | Pro | Val | Val | Gln | Lys | Ser | Ser | Thr | Lys | Pro | Ala | Ala | Gln | Pro |
| | | 265 | | | | | 270 | | | | | 275 | | | |

930

| | | | | | | | | | | | | | | | |
|---|---|---|---|---|---|---|---|---|---|---|---|---|---|---|---|
| GAG | CCT | ACT | AAG | CCC | GCC | GAC | AAG | CCC | CAG | ACC | GAC | AAG | CCT | GTC | GCC |
| Glu | Pro | Thr | Lys | Pro | Ala | Asp | Lys | Pro | Gln | Thr | Asp | Lys | Pro | Val | Ala |
| | 280 | | | | | 285 | | | | | 290 | | | | |

978

| | | | | | | | | | | | | | | | |
|---|---|---|---|---|---|---|---|---|---|---|---|---|---|---|---|
| ACC | AAG | CCT | GCT | GCT | ACC | AAG | CCC | GTC | CAA | CCT | GTC | AAC | AAG | CCC | AAG |
| Thr | Lys | Pro | Ala | Ala | Thr | Lys | Pro | Val | Gln | Pro | Val | Asn | Lys | Pro | Lys |
| 295 | | | | | 300 | | | | | 305 | | | | | 310 |

1026

| | | | | | | | | | | | | | | | |
|---|---|---|---|---|---|---|---|---|---|---|---|---|---|---|---|
| ACA | ACC | CAG | AAG | GTC | CGT | GGA | ACC | AAA | ACC | CGA | GGA | AGC | TGC | CCG | GCC |
| Thr | Thr | Gln | Lys | Val | Arg | Gly | Thr | Lys | Thr | Arg | Gly | Ser | Cys | Pro | Ala |
| | | | | 315 | | | | | 320 | | | | | 325 | |

1074

| | | | | | | | | | | | | | | | |
|---|---|---|---|---|---|---|---|---|---|---|---|---|---|---|---|
| AAG | ACT | GAC | GCT | ACC | GCC | AAG | GCC | TCC | GTT | GTC | CCT | GCT | TAT | TAC | CAG |
| Lys | Thr | Asp | Ala | Thr | Ala | Lys | Ala | Ser | Val | Val | Pro | Ala | Tyr | Tyr | Gln |
| | | | 330 | | | | | 335 | | | | | 340 | | |

1122

| | | | | | | | | | | | | | | | |
|---|---|---|---|---|---|---|---|---|---|---|---|---|---|---|---|
| TGT | GGT | GGT | TCC | AAG | TCC | GCT | TAT | CCC | AAC | GGC | AAC | CTC | GCT | TGC | GCT |
| Cys | Gly | Gly | Ser | Lys | Ser | Ala | Tyr | Pro | Asn | Gly | Asn | Leu | Ala | Cys | Ala |
| | | 345 | | | | | 350 | | | | | 355 | | | |

1170

| | | | | | | | | | | | | | | | |
|---|---|---|---|---|---|---|---|---|---|---|---|---|---|---|---|
| ACT | GGA | AGC | AAG | TGT | GTC | AAG | CAG | AAC | GAG | TAC | TAC | TCC | CAG | TGT | GTC |
| Thr | Gly | Ser | Lys | Cys | Val | Lys | Gln | Asn | Glu | Tyr | Tyr | Ser | Gln | Cys | Val |
| | 360 | | | | | 365 | | | | | 370 | | | | |

1218

| | | | | | | | |
|---|---|---|---|---|---|---|---|
| CCC | AAC | TAAATGGTAG | ATCCATCGGT | TGTGGAAGAG | ACTATGCGTC | TCAGAAGGGA | |
| Pro | Asn | | | | | | |
| 375 | | | | | | | |

1274

TCCTCTCATG AGCAGGCTTG TCATTGTATA GCATGGCATC CTGGACCAAG TGTTCGACCC    1334

TTGTTGTACA TAGTATATCT TCATTGTATA TATTTAGACA CATAGATAGC CTCTTGTCAG    1394

CGACAACTGG CTACAAAAGA CTTGGCAGGC TTGTTCAATA TTGACACAGT TTCCTCCATA    1454

AAAAAAAAAA AAAAAAAA    1473

( 2 ) INFORMATION FOR SEQ ID NO:4:

( i ) SEQUENCE CHARACTERISTICS:
        ( A ) LENGTH: 376 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Arg | Ser | Tyr | Thr | Leu | Leu | Ala | Leu | Ala | Gly | Pro | Leu | Ala | Val | Ser |
| 1 | | | | 5 | | | | | 10 | | | | | 15 | |

| | | | | | | | | | | | | | | |
|---|---|---|---|---|---|---|---|---|---|---|---|---|---|---|
| Ala | Ala | Ser | Gly | Ser | Gly | His | Ser | Thr | Arg | Tyr | Trp | Asp | Cys | Cys | Lys |
| | | | 20 | | | | | 25 | | | | | 30 | | |

| | | | | | | | | | | | | | | |
|---|---|---|---|---|---|---|---|---|---|---|---|---|---|---|
| Pro | Ser | Cys | Ser | Trp | Ser | Gly | Lys | Ala | Ala | Val | Asn | Ala | Pro | Ala | Leu |
| | | 35 | | | | | 40 | | | | | 45 | | | |

| | | | | | | | | | | | | | | |
|---|---|---|---|---|---|---|---|---|---|---|---|---|---|---|
| Thr | Cys | Asp | Lys | Asn | Asp | Asn | Pro | Ile | Ser | Asn | Thr | Asn | Ala | Val | Asn |
| | 50 | | | | | 55 | | | | | 60 | | | | |

| | | | | | | | | | | | | | | |
|---|---|---|---|---|---|---|---|---|---|---|---|---|---|---|
| Gly | Cys | Glu | Gly | Gly | Gly | Ser | Ala | Tyr | Ala | Cys | Thr | Asn | Tyr | Ser | Pro |
| 65 | | | | | 70 | | | | | 75 | | | | | 80 |

| | | | | | | | | | | | | | | |
|---|---|---|---|---|---|---|---|---|---|---|---|---|---|---|
| Trp | Ala | Val | Asn | Asp | Glu | Leu | Ala | Tyr | Gly | Phe | Ala | Ala | Thr | Lys | Ile |
| | | | | 85 | | | | | 90 | | | | | 95 | |

| | | | | | | | | | | | | | | |
|---|---|---|---|---|---|---|---|---|---|---|---|---|---|---|
| Ser | Gly | Gly | Ser | Glu | Ala | Ser | Trp | Cys | Cys | Ala | Cys | Tyr | Ala | Leu | Thr |
| | | | 100 | | | | | 105 | | | | | 110 | | |

| | | | | | | | | | | | | | | |
|---|---|---|---|---|---|---|---|---|---|---|---|---|---|---|
| Phe | Thr | Thr | Gly | Pro | Val | Lys | Gly | Lys | Lys | Met | Ile | Val | Gln | Ser | Thr |
| | | 115 | | | | | 120 | | | | | 125 | | | |

| | | | | | | | | | | | | | | |
|---|---|---|---|---|---|---|---|---|---|---|---|---|---|---|
| Asn | Thr 130 | Gly | Gly | Asp | Leu | Gly 135 | Asp | Asn | His | Phe | Asp 140 | Leu | Met | Met | Pro |
| Gly 145 | Gly | Gly | Val | Gly | Ile 150 | Phe | Asp | Gly | Cys | Thr 155 | Ser | Glu | Phe | Gly | Lys 160 |
| Ala | Leu | Gly | Gly | Ala 165 | Gln | Tyr | Gly | Gly | Ile 170 | Ser | Ser | Arg | Ser | Glu 175 | Cys |
| Asp | Ser | Tyr | Pro 180 | Glu | Leu | Leu | Lys | Asp 185 | Gly | Cys | His | Trp | Arg 190 | Phe | Asp |
| Trp | Phe | Glu 195 | Asn | Ala | Asp | Asn | Pro 200 | Asp | Phe | Thr | Phe | Glu 205 | Gln | Val | Gln |
| Cys | Pro 210 | Lys | Ala | Leu | Leu | Asp 215 | Ile | Ser | Gly | Cys | Lys 220 | Arg | Asp | Asp | Asp |
| Ser 225 | Ser | Phe | Pro | Ala | Phe 230 | Lys | Val | Asp | Thr | Ser 235 | Ala | Ser | Lys | Pro | Gln 240 |
| Pro | Ser | Ser | Ser | Ala 245 | Lys | Lys | Thr | Thr | Ser 250 | Ala | Ala | Ala | Ala | Ala 255 | Gln |
| Pro | Gln | Lys | Thr 260 | Lys | Asp | Ser | Ala | Pro 265 | Val | Val | Gln | Lys | Ser 270 | Ser | Thr |
| Lys | Pro | Ala 275 | Ala | Gln | Pro | Glu | Pro 280 | Thr | Lys | Pro | Ala | Asp 285 | Lys | Pro | Gln |
| Thr | Asp 290 | Lys | Pro | Val | Ala | Thr 295 | Lys | Pro | Ala | Ala | Thr 300 | Lys | Pro | Val | Gln |
| Pro 305 | Val | Asn | Lys | Pro | Lys 310 | Thr | Thr | Gln | Lys | Val 315 | Arg | Gly | Thr | Lys | Thr 320 |
| Arg | Gly | Ser | Cys | Pro 325 | Ala | Lys | Thr | Asp | Ala 330 | Thr | Ala | Lys | Ala | Ser 335 | Val |
| Val | Pro | Ala | Tyr 340 | Tyr | Gln | Cys | Gly | Gly 345 | Ser | Lys | Ser | Ala | Tyr 350 | Pro | Asn |
| Gly | Asn | Leu 355 | Ala | Cys | Ala | Thr | Gly 360 | Ser | Lys | Cys | Val | Lys 365 | Gln | Asn | Glu |
| Tyr | Tyr 370 | Ser | Gln | Cys | Val | Pro 375 | Asn | | | | | | | | |

COMPACT DETERGENT COMPOSITIONS WITH HIGH ACTIVITY CELLULASE

TECHNICAL FIELD

The present invention concerns cellulase-containing granular detergent compositions which are in a "compact" form, i.e. they are of a relatively high density and contain a relatively low amount of inorganic filler salt, compared to conventional detergent compositions. In the detergent compositions herein the cellulase comprises a cellulase of high activity defined by the C14CMC method described herein. Preferably the cellulase-is a specific single-component endoglucanase.

BACKGROUND OF THE INVENTION

The need for detergent compositions which exhibit not only good cleaning properties, but also good fabric-softening performance, and other fabric care benefits, is well-established in the art.

The efficiency of cellulolytic enzymes, i.e. cellulases, in terms of textile cleaning and harshness-reducing agent for fabrics,has been recognized for some time; GB-A-2,075, 028, GB-A-2,095,275 and GB-A-2,094,826, disclose detergent compositions with cellulase for improved cleaning performance; GB-A-1,368,599 discloses the use of cellulase for reducing the harshness of cotton-containing fabrics; U.S. Pat. No. 4,435,307 teaches the use of a cellulolytic enzyme derived from *Humicola insolens* as well as a fraction thereof, designated ACXI, as a harshness-reducing detergent additive.

EP-A-0 269 168 discloses optimized detergent compositions containing cellulase, which are formulated at a mild alkaline pH range and provide combined fabric cleaning, fabric softening, and fabric care performance.

In WO 89109259 have been disclosed cellulase preparations useful for reducing the harshness of cotton-containing fabrics, comprising an endoglucanase component with a high endoase activity and affinity towards cellulose.

The practical exploitation of cellulases has however, been set back by the fact that cellulase preparations such as those disclosed in the above-mentioned prior art documents, are complex mixtures, of which only a certain fraction is effective in the fabric-care context; it was thus difficult to implement cost effective industrial production of cellulase for the detergent industry; and large quantities of such cellulase preparations would need to be applied, in order to obtain the desired effect on fabrics.

Improvements in cellulase production also often have not proven to be sufficiently identifiable in terms of applicability in detergents. Defining a cellulase selection criterium relevant for detergent application of cellulase was made possible by the C14CMC-method disclosed in EP-A-350 098. A minimum of 10% removal of immobilized radioactive labelled carboxymethylcellulose has been found to provide high activity cellulase. A preferred group of cellulase falling under the high activity definition according to the present invention has been disclosed in copending Danish Patent Application No.: 1159/90 filed May 5, 1990. There is disclosed a cellulase preparation consisting essentially of a homogeneous endoglucanase component which is immunoreactive with a monoclonal antibody raised against a partially purified 43kD cellulase derived from *Humicola insolens* DM1800.

The finding that this particular endoglucanase component of cellulase is advantageous for the treatment of cellulose-containing materials now permits to produce the cellulase cost-effectively, e.g. by employing recombinant DNA techniques, and allows to apply only a small quantity of the cellulase preparation, and obtain the desired effect on fabrics.

On the other hand, a new generation of detergent compositions is now being marketed, which can be best pictured as "compact detergents" although they have been given a variety of trade names such as "Ultra", "Supra", "Micro" . . . The particularity of such detergent compositions is their relatively high density compared to conventional detergent compositions, and their ability to achieve the same efficiency than conventional detergent compositions by using a considerably lesser amount of "compact" detergent composition. This particularity is best reflected, in terms of composition, by a relatively low amount of inorganic filler salt. The efficiency of such "compact" detergent compositions is best achieved by eliminating the pre-wash cycle and by using dispersing and diffusing devices, which are put directly in the drum of the washing machine at the start of the main washing cycle.

It is an object of the present invention to provide detergent compositions in a compact form, having a relatively high density and containing a low amount of inorganic filler salt, which exhibit optimum cellulase efficiency.

In EP-A-381 397 has been disclosed the effect of low ionic-strength on enzyme performance, in particular lipase.

It has been surprisingly found however, that the effect of the compact matrix on the selected enzymes of the present invention is much higher than what could be expected from state of the art cellulases such as disclosed in EP-A-381 397.

It is another object of the present invention to provide a method for treating fabrics in a washing machine, comprising the utilization of the present detergent compositions at low levels, for the main wash cycle.

SUMMARY OF THE INVENTION

The present invention relates to granular detergent compositions containing a surface-active agent, a builder, an enzyme, and if desired conventional additives, characterized in that the enzyme comprises a cellulase preparation providing at least 10% removal of immobilized radioactive labelled carboxymethylcellulose according to the C14CMC-method, at $25 \times 10^{-6}\%$ by weight of cellulase protein in the laundry test solution.

Preferably, the cellulase compound consists essentially of a homogeneous endoglucanase component which is immunoreactive with a monoclonal antibody raised against a partially purified about ≈43kD cellulase derived from *Humicola insolens*, DSM 1800, or which is homologous to said ≈43kD endoglucanase.

DETAILED DESCRIPTION OF THE INVENTION

The present detergent compositions are in granular form and are characterized by their density, which is higher than the density of conventional detergent compositions. The density of the compositions herein ranges from 550 to 950 g/liter, preferably 650 to 850 g/liter of composition, measured at 20° C.

The "compact" form of he compositions herein is best reflected, in terms of composition, by the amount of inorganic filler salt; inorganic filler salts are conventional ingredients of detergent oppositions in powder form; In conventional detergent compositions, the filler salts are present in substantial amounts, typically 17–35% by weight of the total composition.

In the present compositions, the filler salt is present in amounts not exceeding 15% of the total composition, preferably no exceeding 10%, most preferably not exceeding 5% by weight of the composition.

Inorganic filler salts, such as meant in the present compositions are selected from the alkali and alkaline-earth-metal salts of sulphates and chlorides.

A preferred filler salt is sodium sulphate.

SURFACTANT

A wide range of surfactants can be used in the detergent compositions. A typical listing of anionic, nonionic, ampholytic and zwitterionic classes, and species of these surfactants, is given in U.S. Pat. No. 3,664,961 issued to Norris on May 23, 1972.

Mixtures of anionic surfactants are particularly suitable herein, especially mixtures of sulphonate and sulphate surfactants in a weight ratio of from 5:1 to 1:2, preferably from 3:1 to 2:3, more preferably from 3:1 to 1:1. Preferred sulphonates include alkyl benzene sulphonates having from 9 to 15, especially 11 to 13 carbon atoms in the alkyl radical, and alphasulphonated methyl fatty acid esters in which the fatty acid is derived from a $C_{12}$–$C_{18}$ fatty source preferably from a $C_{16}$–$C_{18}$ fatty source. In each instance the cation is an alkali metal, preferably sodium. Preferred sulphate surfactants are alkyl sulphates having from 12 to 18 carbon atoms in the alkyl radical, optionally in admixture with ethoxy sulphates having from 10 to 20, preferably 10 to 16 carbon atoms in the alkyl radical and an average degree of ethoxylation of 1 to 6. Examples of preferred alkyl sulphates herein are tallow alkyl sulphate, coconut alkyl sulphate, and $C_{14-15}$ alkyl sulphates. The cation in each instance is again an alkali metal cation, preferably sodium.

One class of nonionic surfactants useful in the present invention are condensates of ethylene oxide with a hydrophobic moiety to provide a surfactant having an average hydrophilic-lipophilic balance (HLB) in the range from 8 to 17, preferably from 9.5 to 13.5, more preferably from 10 to 12.5. The hydrophobic (lipophilic) moiety may be aliphatic or aromatic in nature and the length of the polyoxyethylene group which is condensed with any particular hydrophobic group can be readily adjusted to yield a water-soluble compound having the desired degree of balance between hydrophilic and hydrophobic elements.

Especially preferred nonionic surfactants of this type are the $C_9$–$C_{15}$ primary alcohol ethoxylates containing 3–8 moles of ethylene oxide per mole of alcohol, particularly the $C_{14}$–$C_{15}$ primary alcohols containing 6–8 moles of ethylene oxide per mole of alcohol and the $C_{12}$–$C_{14}$ primary alcohols containing 3–5 moles of ethylene oxide per mole of alcohol.

Another class of nonionic surfactants comprises alkyl polyglucoside compounds of general formula $$RO(C_nH_{2n}O)_tZ_x$$

wherein Z is a moiety derived from glucose; R is saturated hydrophobic alkyl group that contains from 12 to 18 carbon atoms; t is from 0 to 10 and n is 2 or 3; x is from 1.3 to 4, the compounds including less than 10% unreacted fatty alcohol and less than 50% short chain alkyl polyglucosides. Compounds of this type and their use in detergent are disclosed in EP-B 0 070 077, 0 075 996 and 0 094 118.

Also suitable as nonionic surfactants are poly hydroxy fatty acid amide surfactants of the formula $R^2$ $$-\underset{O}{C}-\underset{R^1}{N}-Z,$$

wherein $R^1$ is H, $C_{1-4}$ hydrocarbyl, 2-hydroxy ethyl, 2-hydroxy propyl or a mixture thereof, $R_2$ is $C_{5-31}$ hydrocarbyl, an Z is a polyhydroxyhydrocarbyl having a linear hydrocarbyl chain with at least 3 hydroxyls directly connected to the chain, or an alkoxylated derivative thereof. Preferably, $R_1$ is methyl, $R_2$ is a straight. $C_{11-15}$ alkyl or alkenyl chain such as coconut alkyl or mixtures thereof, and Z is derived from a reducing sugar such as glucose, fructose, maltose, lactose, in a reductive amination reaction.

A further class of surfactants are the semi-polar surfactants such as amine oxides. Suitable amine oxides are selected from mono $C_8$–$C_{20}$, preferably $C_{10}$–$C_{14}$ N-alkyl or alkenyl amine oxides and propylene-1,3-diamine dioxides wherein the remaining N positions are substituted by methyl, hydroxyethyl or hydroxypropyl groups.

Another class of surfactants are amphoteric surfactants, such as polyamine-based species.

Cationic surfactants can also be used in the detergent compositions herein and suitable quaternary ammonium surfactants are selected from mono $C_8$–$C_{16}$, preferably $C_{10}$–$C_{14}$ N-alkyl or alkenyl ammonium surfactants wherein remaining N positions are substituted by methyl, hydroxyethyl or hydroxypropyl groups.

Mixtures of surfactant types are preferred, more especially anionic-nonionic and also anionic-nonionic-cationic mixtures. Particularly preferred mixtures are described in British Patent No. 2040987 and European Published Application No. 0 087 914. The detergent compositions can comprise from 1%–70% by weight of surfactant, but usually the surfactant is present in the compositions herein an amount of from 1% to 30%, more preferably from 10–25% by weight.

BUILDER

Builder materials will typically be present at from 10% to 60% of the detergent compositions herein. The compositions herein are free or substantially free of phosphate-containing builders (substantially free being herein defined to constitute less than 1% of the total detergent builder system), and the builder system herein consists of water-soluble builders, water-insoluble builders, or mixtures thereof.

Water insoluble builders can be an inorganic ion exchange material, commonly an inorganic hydrated aluminosilicate material, more particularly a hydrated synthetic zeolite such as hydrated Zeolite A, X, B or HS.

Preferred aluminosilicate ion-exchange materials have the unit cell formula $$M_z[(AlO_2)_z(SiO_2)_y]xH_2O$$

wherein M is a calcium-exchange cation, z and y are at least 6; the molar ratio of z to y is from 1.0 to 0.5 and x is at least 5, preferably from 7.5 to 276, more preferably from 10 to 264. The aluminosilicate materials are in hydrated form and are preferably crystalline containing from 10% to 28%, more preferably from 18% to 22% water.

The above aluminosilicate ion exchange materials are further charaterized by a particle size diameter of from 0.1 to 10 micrometers, preferably from 0.2 to 4 micrometers. The term "particle size diameter" herein represents the average particle size diameter of a given ion exchange material as determined by conventional analytical techniques such as, for example, microscopic determination utilizing a scanning electron microscope. The aluminosilicate ion exchange materials are further characterized by their calcium ion exchange capacity, which is at least 200 mg equivalent of $CaCO_3$ water hardness/g of aluminosilicate, calculated on an anhydrous basis, and which generally is in the range of from 300 mg eq./g to 352 mg eq./g. The aluminosilicate ion exchange materials herein are still further characterized by their calcium ion exchange rate which is described in detail in GB-1,429,143.

Aluminosilicate ion exchange materials useful in the practice of this invention are commercially available and can be naturally occurring materials, but are preferably synthetically derived. A method for producing aluminosilicate ion exchange materials is discussed in U.S. Pat. No. 3,985,669. Preferred synthetic crystalline aluminosilicate ion exchange materials useful herein are available under the designation Zeolite A, Zeolite B, Zeolite X, Zeolite HS and mixtures thereof. In an especially preferred embodiment, the crystalline aluminosilicate ion exchange material is Zeolite A and has the formula $$Na_{12}[(AlO_2)_{12}(SiO_2)_{12}]xH_2O$$

wherein x is from 20 to 30, especially 27. Zeolite X of formula $Na_{86}[(AlO_2)_{86}(SiO_2)_{106}]\cdot 10.276H_2O$ is also suitable, as well as Zeolite HS of formula $Na_6[(AlO_2)_6(SiO_2)_6]\cdot 7.5\ H_2O$).

Another suitable water-insoluble, inorganic builder material is layered silicate, e.g. SKS-6 (Hoechst). SKS-6 is a crystalline layered silicate consisting of sodium silicate ($Na_2Si_2O_5$). The high $Ca^{++}/Mg^{++}$ binding capacity is mainly a cation exchange mechanism. In hot water, the material becomes more soluble.

The water-soluble builder can be a monomeric or oligomeric carboxylate chelating agent.

Suitable carboxylates containing one carboxy group include lactic acid, glycollic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenlegenschrift 2,446,686, and 2,446,687 and U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2-ethane tetracarboxylates, 1,1,3,3-propane tetracarboxylates and 1,1,2,3-propane tetracarboxylates. Polycarboxylates containing sulfo substituents include the sulfosuccinate derivatives disclosed in British Patent Nos. 1,398,421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis,cis-tetacarboxylates, cyclopentadienide pentacarboxylates, 2,3,4,5-tetrahydrofuran-cis, cis, cis-tetracarboxylates, 2,5-tetrahydrofuran-cis-dicarboxylates, 2,2,5,5-tetrahydrofuran-tetracarboxylates, 1,2,3,4,5,6-hexanehexacarboxylates and and carboxymethyl derivatives of polyhydric alcohols such as sorbitol, mannitol and xylitol. Aromatic polycarboxylates include mellitic acid, pyromellitic acid and the phtalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A, and a water-soluble carboxylate chelating agent such as citric acid.

Other builder materials that can form part of the builder system for the purposes of the invention include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated from each other by not more than two carbon atoms.

Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

CELLULASE

The activity of enzymes and particularly the activity of cellulase enzyme has been defined for various applications by different analytical methods. These methods all attempt to provide a realistic assessment of the expected use performance or at least a measurement correlating with the in use performance. As has been detailed in European Patent Application EP-A-350098, many of the methods, particularly these frequently used by cellulase manufacturers, are not sufficiently correlated with the in use performance of cellulase in laundry detergent compositions. This is due to the various other usage conditions for which these activity measurement methods have been developed.

The method described in EP-A-350098, has been developed to be and to have a predictive correlation for the ranking of cellulase activity in laundry detergent compositions.

The present invention therefore uses the method disclosed in EP-A-350098 to screen cellulases in order to distinguish cellulases which are useful in the present invention and those which would not provide the objectives of the present invention. The screening method, hereinafter referred to as C14CMC-Method, which has been adopted from the method disclosed in EP-A-350098, can be described as follows:

Principle:

The principle of the C14CMC-Method for screening is to measure at a defined cellulase concentration in a wash solution the removal of immobilized carboxy methyl cellulose (CMC) from a cloth substrate. The removal of CMC is measured by radio-active labelling of some of the CMC by using C14 radio-active carbon. Simple counting of the amount of radio-active C14 on the cloth substrate before and after the cellulase treatment allows the evaluation of the cellulase activity.

Sample preparation:

CMC preparation:

The radio-active CMC stock solution is prepared according to Table I. The radio-active CMC can be obtained by methods referred to in EP-A-350098.

Fabric substrates:

The fabric substrates are muslin cotton swatches having a size of 5 cm×5 cm. They are inocculated with 0.35 ml of the radio-active labelled CMC stock solution in their center. The muslin cotton swatches are then airdried.

Immobilization of CMC:

To immobilize the radio-active labelled CMC on the muslin cotton swatches, laundero-meter equipment "Linitest Original Haunau" made by Original Haunau, Germany, is used. A metal jar of the laundero-meter is filled with 400 ml of hard water (4 mmol/liter of $Ca^{++}$ ions). A maximum number of 13 swatches can be used per jar. The jar is then incubated in a heat-up cycle from 20° C. to 60° C. over 40 minutes in the laundero-meter equipment. After incubation the swatches are rinsed under running city water for 1 minute. They are squeezed and allowed to airdry for at least 30 minutes.

According to EP-A-350098 samples of the swatches with immobilized radio-active CMC can also be measured as "blank samples" without washing.

Sample treatment:
Laundry test solution:

The laundry test solution is prepared according to the composition of Table II. It is balanced to pH 7.5. The laundry test solution is the basis to which a cellulase test sample is added. Care should be taken to not dilute the laundry test solution by adding water to a 100% balance prior to having determined the amount of cellulase to be added. The amount of cellulase which is used in this screening test should be added to provide $25 \times 10^{-6}$ weight percent of cellulase protein in the laundry test solution (equivalent to 0.25 milligram/liter at 14.5° C.).

Wash procedure:

The swatches thus inocculated with radio-active labelled CMC are then treated in a laundry simulation process. The laundry process is simulated in the laundero-meter type equipment, "Linitest, Original Haunau", by Original Haunau, Haunau Germany. An individual swatch is put into a 20 $cm^3$ glass vial. The vial is filled with 10 ml of the laundry test solution and then sealed liquid tight. Up to 5 vials are put into each laundero-meter jar. The jar is filled with water as a heat tranfer medium for the laundering simulation. The laundering simulation is conducted as a heat-up cycle from 20° C. to 60° C. over 40 minutes.

After the processing of the samples the vials are submerged in cold water and subsequently each swatch is taken out of its vial, rinsed in a beaker under running soft water, squeezed and allowed to airdry for at least 30 minutes.

Measurement:

In order to measure radio-active labelled CMC removal, a scintillation counter, for example, a LKB 1210 Ultrabeta Scintillation Counter, is used. In order to obtain most accurate results, the instruction manual for optimum operation of the particular scintillation counter should be followed. For example, for the LKB 1210 Ultrabeta Scintillation Counter, the following procedure should be followed. The swatch to be measured is put into a plastic vial filled with 12 ml of scintillator liquid (e.g. scintillator 299 from Packard). The swatch is then allowed to stabilize for at least 30 minutes. The vial is then put into the LKB 1210 Ultrabeta Scintillation Counter and the respective radio-activity counts for the swatch is obtained.

In order to measure the amount of CMC removal due only to the cellulase, a measurement of a swatch which has been inocculated at the same time but has been treated in the laundry test solution without cellulase, is necessary. The activity of the cellulase is then expressed as percent of radio-active labelled CMC removal. This percentage is calculated by the following formula:

$$\% \text{ of radio-active } CMC \text{ removal} = \frac{XO - XC}{XO} \times 100$$

Wherein

XO is the radioactivity scintillation count of a swatch treated with the laundry test solution without cellulase XC is the radioactivity scintillation count of a swatch treated with the laundry test solution containing the cellulase to be evaluated Statistical considerations, procedure confirmation:

In order to provide statistically sound results, standard statistical analysis should be employed. For the given example, using the LKB 1210 Ultrabeta Scintillation Counter, it has been found that a sample size of 3 swatches for each radioactivity scintillation count can be used.

In order to confirm the procedure by internal crosschecking, measurement and calculation of the "blank sample" according to EP-A-350098 are recommended. This will allow to detect and eliminate errors.

Interpretation of results:

The described screening test does provide a fast, unique and reliable method to identify cellulases which satisfy the activity criteria of the present invention versus cellulases which are not part of the present invention.

It has been found that a removal of 10% or more of the immobilized radioactive labelled CMC according to the above C14CMC-method, indicates that the respective cellulase satisfies the requirements of the invention.

It will be obvious to those skilled in the art that removal percentages above 10% indicate a higher activity for the respective cellulase. It therefore is contemplated that cellulase providing above 25% or preferably above 50% removal of radioactive labelled CMC, at the protein concentration in the laundry test solution according to the C14CMC-method, would provide indication of an even better performance of the cellulase for use in laundry detergents.

It also has been contemplated that usage of higher concentrations of cellulase for C14CMC-method, would provide higher removal percentages. However, there exists no linear proven correlation between cellulase concentration- and removal percentage obtained by it.

It also has been contemplated that usage of higher concentrations of cellulase for C14CMC-method, would provide higher removal percentages.

TABLE I

| Radioactive $C_{14}$ labelled CMC stock solution (all percentages by weight of total solution) | |
|---|---|
| Total CMC* (CMC should be detergent grade CMC with a degree of substitution from about 0.47 to about 0.7) | $99.2 \times 10^{-3}\%$ |
| Ethanol | $14985.12 \times 10^{-3}\%$ |
| Deionized Water | $84915.68 \times 10^{-3}\%$ |
| Total: | 100% |

*Total CMC contains non-radio-active and radio-active CMC to provide a radio-activity which allows sufficiently clear readings on the scintillation counter used. For example, the radio-active CMC can have an activity of 0.7 millicurie/g and be mixed

TABLE II

Laundry test solution
(all percentages by weight of total solution)

| | |
|---|---|
| Linear $C_{12}$ alkyl benzene sulphonic acid | 0.110% |
| Coconut alkyl sulphate (TEA salt) | 0.040% |
| $C_{12-15}$ alcohol ethoxylate (E07) | 0.100% |
| Coconut fatty acid | 0.100% |
| Oleic acid | 0.050% |
| Citric acid | 0.010% |
| Triethanolamine | 0.040% |
| Ethanol | 0.060% |
| Propanediol | 0.015% |
| Sodium hydroxide | 0.030% |
| Sodium formate | 0.010% |
| Protease | 0.006% |
| Water (2.5 mmol/liter $Ca^{++}$), pH adjustment agent (HCL or NaOH solutions) and cellulase | balance to 100% |

According to the present invention, preferred cellulase are those as described in Danish Patent Application 1159/90. For example, a cellulase preparation useful in the compositions of the invention can consist essentially of a homogeneous endoglucanase component, which is immunoreactive with an antibody raised against a highly purified 43kD cellulase derived from *Humicola insolens*, DSM 1800, or which is homologous to said 43kD endoglucanase.

It should be stressed that all cellulase enzymes according to the present invention have to meet the criteria of the above mentioned screening test. However, in the Danish Patent Application 1159/90 additional criteria are established allowing to identify preferred cellulase enzymes in combination with the present screening test.

Cellulase preparations particularly useful in the compositions of the invention are those in which in addition to the screening test, the endoglucanase component exhibits a CMC-endoase activity of at least about 50, preferably at least about 60, in particular at least about 90 CMC-endoase units per mg of total protein. In particular, a preferred endoglucanase component exhibits a CMC-endoase activity of at least 100 CMC-endoase units per mg of total protein.

In the present context, the term "CMC-endoase activity" refers to the endoglucanase activity of the endoglucanase component in terms of its ability to degrade cellulose to glucose, cellobiose and triose, as determined by a viscosity decrease of a solution of carboxymethyl cellulose (CMC) after incubation with the cellulase preparation of the invention, as described in detail below.

The CMC-endoase (endoglucanase) activity can be determined from the viscosity decrease of CMC, as follows: A substrate solution is prepared, containing 35 g/l CMC (Hercules 7 LFD) in 0.1M tris buffer at pH 9.0. The enzyme sample to be analyzed is dissolved in the same buffer. 10 ml substrate solution and 0.5 ml enzyme solution are mixed and transferred to a viscosimeter (e.g. Haake VT 181, NV sensor, 181 rpm), thermostated at 40° C. Viscosity readings are taken as soon as possible after mixing and again 30 minutes later. The amount of enzyme that reduces the viscosity to one half under these conditions is defined as 1 unit of CMC-endoase activity.

SDS polyacrylamide gel electrophoresis (SDS-PAGE) and isoelectric focusing with marker proteins in a manner known to persons skilled in the art were used to determine the molecular weight and isolelectric point (pI), respectively, of the endoglucanase component in the cellulase preparation useful in the present context. In this way, the molecular weight of a specific endoglucanase component was determine to be 43kD. The isoelectric point of this endoglucanase was determined to be about 5.1.

The cellobiohydrolase activity may be defined as the activity towards cellobiose p-nitrophenyl. The activity is determined as umole nitrophenyl released per minute at 37° C. and pH 7.0. The present endoglucanase component was found to have essentially no cellobiohydrolase activity.

The endoglucanase component in the cellulase preparation herein has initially been isolated by extensive purification procedures, i.a. involving reverse phase HPLC purification of a crude *H. insolens* cellulase mixture according to U.S. Pat. No. 4,435,307. This procedure has surprisingly resulted in the isolation of a 43kD endoglucanase as a single component with unexpectedly favourable properties due to a surprisingly high endoglucanase activity.

Also, in addition to the screening test, the cellulase enzymes useful in the present compositions can further be defined as enzymes exhibiting endoglucanase activity (in the following referred to as an "endoglucanase enzyme"), which enzymes have the amino acid sequence shown in the appended Sequence Listing ID#2, or a homologue thereof exhibiting endoglucanase activity.

In the present context, the term "homologue" is intended to indicate a polypeptide encoded by DNA which hybridizes to the same probe as the DNA coding for the endoglucanase enzyme with this amino acid sequence under certain specified conditions (such as presoaking in 5×SSC and prehybridizing for 1 h at 40° C. in a solution of 20% formamide, 5×Denhardt's solution, 50 mM sodium phosphate, pH 6.8, and 50 ug of denatured sonicated calf thymus DNA, followed by hybridization in the same solution supplemented with 100 uM ATP for 18 h at 40° C.). The term is intended to include derivatives of the aforementioned sequence obtained by addition of one or more amino acid residues to either or both the C- and N-terminal of the native sequence, substitution of one or more amino acid residues at one or more sites in the native sequence, deletion of one or more amino acid residues at either or both ends of the native amino acid sequence or at one or more sites within the native sequence, or insertion of one or more amino acid residues at one or more sites in the native sequence.

The endoglucanase enzyme herein may be one producible by species of Humicola such as *Humicola insolens* e.g. strain DSM 1800, deposited on Oct. 1, 1981 at the Deutsche Sammlung von Mikroorganismen, Mascheroder Weg 1B, D-3300 Braunschweig, FRG, in accordance with the provisions of the Budapest Treaty on the International Recognition of the Deposit of Microorganisms for the Purposes of Patent Procedure (the Budapest Treaty).

In still a further aspect, the cellulase enzymes useful herein can be defined, in addition to the screening test, as endoglucanase enzymes which have the amino acid sequence shown in the appended Sequence Listing ID#4, or a homologue thereof (as defined above) exhibiting endoglucanase activity. Said endoglucanase enzyme may be one producible by a species of Fusarium, such as *Fusarium oxysporum*, e.g. strain DSM 2672, deposited on Jun. 6, 1983 at the Deutsche Sammlung von Mikroorganismen, Mascheroder Weg 1B, D-3300 Braunschweig, FRG, in accordance with the provisions of the Budapest Treaty.

Furthermore, it is contemplated that homologous endoglucanases may be derived from other microorganisms producing cellulolytic enzymes, e.g. species of Trichoderma, Myceliophthora, Phanerochaete, Schizophyllum, Penicillium, Aspergillus, and Geotricum.

For industrial production of the cellulase preparation herein, however, it is preferred to employ recombinant DNA techniques or other techniques involving adjustements of fermentations or mutation of the microorganisms involved to ensure overproduction of the desired enzymatic activities. Such methods and techniques are known in the art and may readily be carried out by persons skilled in the art.

The endoglucanase component may thus be one which is producible by a method comprising cultivating a host cell transformed with a recombinant DNA vector which carries a DNA sequence encoding said endoglucanase component or a precursor of said endoglucanase component as well as DNA sequences encoding functions permitting the expression of the DNA sequence encoding the endoglucanase component or precursor thereof, in a culture medium under conditions permitting the expression of the endoglucanase component or precursor thereof and recovering the endoglucanase component from the culture.

DNA constructs comprising a DNA sequence encoding an endoglucanase enzyme as described above, or a precursor form of the enzyme, include the DNA constructs having a DNA sequence as shown in the appended Sequence Listings ID#1 or ID#3, or a modification thereof. Examples of suitable mofidications of the DNA sequence are nucleotide substitutions which do not give rise to another amino acid sequence of the endoglucanase, but which correspond to the codon usage of the host organism into which the DNA construct is introduced or nucleotide substitutions which do give rise to a different amino acid sequence and therefore, possibly, a different protein structure which might give rise to an endoglucanase mutant with different properties than the native enzyme. Other examples of possible modifications are insertion of one or more nucleotides at either end of the sequence, or deletion of one or more nucleotides at either end or within the sequence.

DNA constructs encoding endoglucanase enzymes useful herein may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *EMBO Journal* 3, 1984, pp. 801–805. According to the phosphoamidite method, oligonucleotides are synthesized, e.g. in an automatic DNA synthesizer, purified, annealed, ligated and cloned in suitable vectors.

A DNA construct encoding the endoglucanase enzyme or a precursor thereof may, for instance, be isolated by establishing a cDNA or genomic library of a cellulase-producing microorganism, such as *Humicola insolens*, DSM 1800, and screening for positive clones by conventional procedures such as by hybridization using oligonucleotide probes synthesized on the basis of the full or partial amino acid sequence of the endoglucanase in accordance with standard techniques (cf. Sambrook et al., *Molecular Cloning: A Laboratory Manual*, 2nd. Ed. Cold Spring Harbor, 1989), or by selecting for clones expressing the appropriate enzyme activity (i.e. CMC-endoase activity as defined above), or by selecting for clones producing a protein which is reactive with an antibody against a native cellulase (endoglucanase).

Finally, the DNA construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire DNA construct, in accordance with standard techniques. The DNA construct may also be prepared by polymerase chain reaction using specific primers, for instance as described in U.S. Pat. No. 4,683,202 or R. K. Saiki et al., *Science* 239, 1988, pp. 487–491.

Recombinant expression vectors into which the above DNA constructs are inserted include any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into wich it has been integrated.

In the vector, the DNA sequence encoding the endoglucanase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the endoglucanase, the promoter and the terminator, respectively, and to insert them into suitable vectors are well known to persons skilled in the art (cf., for instance, Sambrook et al., op.cit.).

Host cells which are transformed with the above DNA constructs or the above expression vectors may be for instance belong to a species of Aspergillus, most preferably *Aspergillys oryzae* or *Aspergillus niger*. Fungal cells may be transformed by a process involving protoplast formation and transformation of the protoplasts followed by regeneration of the cell wall in a manner known per se. The use of Aspergillus as a host microorganism is described in EP 238 023 (of Novo Industri A/S), the contents of which are hereby incorporated by reference. The host cell may also be a yeast cell, e.g. a strain of *Saccharomyces cerevisiae*.

Alternatively, the host organism may be a bacterium, in particular strains of Streptomyces and Bacillus, and *E. coli*. The transformation of bacterial cells may be performed according to conventional methods, e.g. as described in Sambrook et al., *Molecular Cloning: A Laboratory Manual*, Cold Spring Harbor, 1989.

The screening of appropriate DNA sequences and construction of vectors may also be carried out by standard procedures, cf. Sambrook et al., op.cit.

The medium used to cultivate the transformed host cells may be any conventional medium suitable for growing the host cells in question. The expressed endoglucanase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

By employing recombinant DNA techniques as indicated above, techniques of protein purification, techniques of fermentation and mutation or other techniques which are well known in the art, it is possible to provide endoglucanases of a high purity.

The level in the present composition of cellulase described above should be such that the amount of enzyme protein to be delivered in the wash solution is from 0.005 to 40 mg/liter of wash solution, preferably 0.01 to 10 mg/liter of wash solution.

OPTIONAL INGREDIENTS

The present compositions will typically include optional ingredients that normally form part of detergent compositions Antiredeposition and soil suspension agents, optical brighteners, bleaches, bleach activators, suds suppressors, anticacking agents, dyes and pigments are examples of such optional ingredients and can be added in varying amounts as desired.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably from 0.75% to 8%, most preferably from 1% to 6% by weight of the composition.

Preferred optical brighteners are anionic in character, examples of which are disodium 4,4$^1$-bis-(2-diethanolamino-4-anilino-s-triazin-6-ylamino)stilbene-2:2$^1$ disulphonate, disodium 4, -4$^1$-bis-(2-morpholino-4-anilino-s-triazin-6-ylamino)stilbene-2:2$^1$-disulphonate, disodium 4,4$^1$-bis-(2,4-dianilino-s-triazin-6-ylamino)stilbene-2:2$^1$-disulphonate, monosodium 4$^1$,4$^{11}$-bis-(2,4-dianilino-s-triazin-6-ylamino)stilbene-2-sulphonate, disodium 4,4$^1$-bis-(2-anilino-4-(N-methyl-N-2- hydroxyethylamino)-s-triazin-6-ylamino)stilbene-2,2$^1$-disulphonate, disodium 4,4$^1$-bis-(4-phenyl-2,1,3-triazol-2-yl)-stilbene-2,2$^1$ disulphonate, disodium 4,4$^1$bis(2-anilino-4-(1-methyl-2-hydroxyethylamino)-s-triazin-6-ylamino)stilbene-2,2$^1$disulphonate and sodium 2(stilbyl-4$^{11}$-(naphtho-1$^1$,2$^1$:4,5)-1,2,3-triazole-2$^{11}$-sulphonate.

Any particulate inorganic perhydrate bleach can be used, in an amount of from 3% to 40% by weight, more preferably from 8% to 25% by weight and most preferably from 12% to 20% by weight of the compositions. Preferred examples of such bleaches are sodium perborate monohydrate and tetrahydrate, percarbonate, and mixtures thereof.

Another preferred separately mixed ingredient is a peroxy carboxylic acid bleach percursor, commonly referred to as a bleach activator, which is preferably added in a prilled or agglomerated form. Examples of suitable compounds of this type are disclosed in British Patent Nos. 1586769 and 2143231 and a method for their formation into a prilled form is described in European Published Patent Application No. 0 062 523. Preferred examples of such compounds are tetracetyl ethylene diamine and sodium 3, 5, 5 trimethyl hexanoyloxybenzene sulphonate.

Bleach activators are normally employed at levels of from 0.5% to 10% by weight, more frequently from 1% to 8% and preferably from 2% to 6% by weight of the composition.

Another optional ingredient is a suds suppressor, exemplified by silicones, and silica-silicone mixtures. Silicones can be generally represented by alkylated polysiloxane materials while silica is normally used in finely divided forms exemplified by silica aerogels and xerogels and hydrophobic silicas of various types. These materials can be incorporated as particulates in which the suds suppressor is advantageously releasably incorporated in a water-soluble or water-dispersible, substantially non-surface-active detergent impermeable carrier. Alternatively the suds suppressor can be dissolved or dispersed in a liquid carrier and applied by spraying on to one or more of the other components.

As mentioned above, useful silicone suds controlling agents can comprise a mixture of an alkylated siloxane, of the type referred to hereinbefore, and solid silica. Such mixtures are prepared by affixing the silicone to the surface of the solid silica. A preferred silicone suds controlling agent is represented by a hydrophobic silanated (most preferably trimethyl-silanated) silica having a particle size in the range from 10 millimicrons to 20 millimicrons and a specific surface area above 50 m$^2$/g intimately admixed with dimethyl silicone fluid having a molecular weight in the range from about 500 to about 200,000 at a weight ratio of silicone to silanated silica of from about 1:1 to about 1:2.

A preferred silicone suds controlling agent is disclosed in Bartollota et al. U.S. Pat. No. 3,933,672. Other particularly useful suds suppressors are the self-emulsifying silicone suds suppressors, described in German Patent Application DTOS 2,646,126 published Apr. 28, 1977. An example of such a compound is DC-544, commercially availably from Dow Corning, which is a siloxane/glycol copolymer.

The suds suppressors described above are normally employed at levels of from 0.001% to 2% by weight of the composition, preferably from 0.01% to 1% by weight. The incorporation of the suds mofidiers is preferably made as separate particulates, and this permits the inclusion therein of other suds controlling materials such as C20–C24 fatty acids, microcrystalline waxes and high MW copolymers of ethylene oxide and propylene oxide which would otherwise adversely affect the dispersibility of the matrix. Techniques for forming such suds modifying particulates are disclosed in the previously mentioned Bartolotta et al U.S. Pat. No. 3,933,672.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in the commonly assigned U.S. Pat. Nos. 4116885 and 4711730 and European Published Patent Application No. 0 272 033. A particular preferred polymer in accordance with EP-A-0 272 033 has the formula

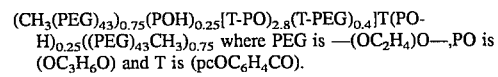

(CH$_3$(PEG)$_{43}$)$_{0.75}$(POH)$_{0.25}$[T-PO)$_{2.8}$(T-PEG)$_{0.4}$]T(POH)$_{0.25}$((PEG)$_{43}$CH$_3$)$_{0.75}$ where PEG is —(OC$_2$H$_4$)O—,PO is (OC$_3$H$_6$O) and T is (pcOC$_6$H$_4$CO).

Certain polymeric materials such as polyvinyl pyrrolidones typically of MW 5000–20000, preferably 10000–15000, also form useful agents in preventing the transfer of labile dyestuffs between fabrics during the washing process.

Fabric softening agents can also be incorporated into detergent compositions in accordance with the present invention. These agents may be inorganic or organic in type. Inorganic softening agents are exemplified by the smectite clays disclosed in GB-A-1,400,898. Organic fabric softening agents include the water-insoluble tertiary amines as disclosed in GB-A-1514276 and EP-B-0 011 340 and their combination with mono C$_{12}$–C$_{14}$ quaternary ammonium salts are disclosed in EP-B-0 026 527 and EP-B-0 026 528 and di-long-chain amides as disclosed in EP-B-0 242 919. Other useful organic ingredients of fabric softening systems include high molecular weight polyethylene oxide materials as disclosed in EP-A-0 299 575 and 0 313 146.

Levels of smectite clay are normally in the range from 5% to 20%, more preferably from 8% to 15% by weight with the material being added as a dry mixed component to the remainder of the formulation. Organic fabric softening agents such as the water-insoluble tertiary amines or di-long-chain amide materials are incorporated at levels of from 0.5% to 5% by weight, normally from 1% to 3% by weight whilst the high molecular weight polyethylene oxide materials and the water-soluble cationic materials are added at levels of from 0.1% to 2%, normally from 0.15% to 1.5%. by weight. These materials are normally added to the spray dried portion of the composition, although in some instances it may be more convenient to add them as a dry mixed particulate, or spray them as a molten liquid on to other solid components of the composition.

Enzymes other than the specific cellulase preparation herein can be present in the composition herein, such as proteases, lipases and amylases.

MAKING PROCESS

Compositions according to the present invention can be made via a variety of methods including dry mixing, spray drying, agglomeration and granulation and combinations of any of these techniques.

PREFERRED MAKING PROCESS

A preferred method of making the compositions herein involves a combination of spray drying, agglomeration in a high speed mixer and dry mixing.

A first granular component containing a relatively insoluble anionic surfactant is spray dried and part of the spray dried product is diverted ad subjected to a low level of nonionic surfactant spray on before being reblended with the remainder. A second granular component is made by dry neutralisation of an anionic surfactant acid using sodium carbonate as the neutralising agent in a continuous high speed blender such as a Lodige KM mixer. The first and second components together with other dry mix ingredients such as the carboxylate chelating agent, inorganic peroxygen bleach, bleach activator, soil suspension agent, silicate and enzyme are then fed to a conveyor belt from which they are transferred to a horizontally rotating drum in which perfume and silicone suds suppressor are sprayed on to the product. In highly preferred compositions, a further drum mixing step is employed in which a low (approx. 2%) level of finely divided crystalline aluminosilicate is introduced to increase density and improve granular flow characteristics.

PROCESS OF WASHING

The compact detergent compositions herein have the ability to achieve the same efficiency than conventional detergent compositions, when a considerably lesser amount of composition herein, is used in the main wash cycle of a washing machine.

Accordingly, in an other embodiment of the invention, it is herewith provided for a process for washing fabrics in a washing machine wherein an amount of from 15 to 170 g of a detergent composition according to the present invention is used for the main wash cycle.

Typically, under European conditions, the recommended usage is from 80 to 140 g of detergent composition for the main wash cycle, without the need of a pre-wash.

The detergent compositions herein are preferably delivered directly to the drum and not indirectly via the outer casing of the machine. This can most easily be achieved by incorporation of the composition in a bag or container from which it can be released at the start of the wash cycle in response to agitation, a rise in temperature or immersion in the wash water in the drum. Such a container will be placed in the drum, together with the fabrics to be washed. Alternatively the washing machine itself may be adapted to permit direct addition of the composition to the drum e.g. by a dispensing arrangement in the access door.

Products comprising a detergent composition enclosed in a bag or container are usually designed in such a way that container integrity is maintained in the dry state to prevent egress of the contents when dry, but are adapted for release of the container contents on exposure to a washing environment, normally on immersion in an aqueous solution.

Usually the container will be flexible, such as a bag or pouch. The bag may be of fibrous construction coated with a water impermeable protective material so as to retain the contents, such as is disclosed in European published Patent Application No. 0 018 678. Alternatively it may be formed of a water insoluble synthetic polymeric material provided with an edge seal or closure designed to rupture in aqueous media as disclosed in European published Patent Application Nos. 0 011 500, 0 011 501, 0 011 502, and 0 011 968. A convenient form of water frangible closure comprises a water soluble adhesive disposed along and sealing one edge of a pouch formed of a water impermeable polymeric film such as polyethylene or polypropylene.

In a variant of the bag or container product form, laminated sheet products can be employed in which a central flexible layer is impregnated and/or coated with a composition and then one or more outer layers are applied to produce a fabric-like aesthetic effect. The layers may be sealed together so s to remain attached during use or may separate on contact with water to facilitate the release of the coated or impregnated material.

An alternative laminate form comprises one layer embossed or deformed to provide a series of pouch-like containers into each of which the detergent components are deposited in measured amounts, with a second layer overlying the first layer and sealted thereto in those areas between the pouch-like containers where the two layers are in contact. The components may be deposited in particulate, paste or molten form and the laminate layers should prevent egress of the contents of the pouch-like containers prior to their addition to water. The layers may separate or may remain attached together on contact with water, the only requirement being that the structure should permit rapid release of the contents of the pouch-like containers into solution. The number of pouch-like containers per unit area of substrate is a matter of choice but will normally vary between 500 and 25,000 per square meter.

Suitable materials which can be used for the flexible laminate layers in this aspect of the invention include, among others, sponges, paper and woven and non-woven fabrics.

However the preferred means of carrying out the washing process according to the present invention includes the use of a reusable dispensing device having walls that are permeable to liquid but impermeable to the solid composition.

Devices of this kind are disclosed in European Patent Application Publication Nos. 0 343 069 and 0 344 070. The latter Application discloses a device comprising a flexible sheet in the form of a bag extending from a support ring defining an orifice, the orifice being adapted to admit to the bag sufficient products for one washing cycle in a washing cycle. A portion of the washing medium flows through the orifice into the bag, dissolves the product, and the solution then passes outwardly through the orifice into the washing medium. The support ring is provided with a masking arrangement to prevent egress of wetted, undissolved, prod-

EXAMPLES

The following examples illustrate the invention and facilitate its understanding.

The abbreviations for the individual ingredients have the following meaning:

LAS: sodium salt of linear dodecyl benzene sulfonate
TAS: sodium salt of tallow alcohol sulfate
AS: sodium salt of alkyl (C14–C15) sulfate
AO: C12–C14 alkyl dimethylamine oxide
FA45E7: fatty alcohol (C14–C15) ethoxylated with about 7 moles of ethylene oxide
CAT: C12 alkyl trimethyl ammonium chloride
Clay: smectite clay
Zeolite 4A: sodium salt of zeolite 4A with average particle size between 1–10 micrometer
SKS-6: crystalline layered silicate (Hoechst)
Copolymer AA/MA: copolymer of acrylic acid and maleic acid
PAA: polyacrylic acid MW 100→10000
CMC: carboxymethylcellulose Phosphonate: sodium salt of ethylenediamine tetramethylene phosphonic acid
EDTA: sodium salt of ethylenediamine tetra acetate
PB1: NaBO2.H2O2
PB4: NaBO2.H2O2.3H2O
TAED: tetra acetyl ethylene diamine
NOBS: - nonanoyl oxybenzene sodium sulfonate
P.A.: sulphonated zinc phthalocyanine Silicate (R=n): SiO2/Na2O=n
Amylase: Termamyl 60 T (Novo-Nordisk)
Lipase: Lipolase 100 T (Novo-Nordisk)
Protease: Savinase 4 T (Novo-Nordisk)
SSS: Suds Suppressing System (silica/silicone mixture)

EXAMPLE I

Criticality of the cellulase performance parameter of claim 1

The following test was conducted:

Test conditions:

Washing temperature: 60° C. (heat up cycle)
Washing time: 40 min.
pH = 7.5
Water hardness: 4 mmol/L
Detergent concentration: 1%
Detergent composition: cfr. EPA 350 098 ex. 1
Cellulases:

1) Celluzyme$^R$ supplied by Novo Nordisk = reference
2) 43kD endoglucanase = cellulase according to the invention

| Test Results: | % C14-CMC Removal by Cellulase |
|---|---|
| Detergent without cellulase (=reference) | 0 |
| Detergent + Celluzyme$^R$ | |
| 0.25 mg protein/L | below 3 |
| 0.9 mg protein/L | 10 |
| 1.5 mg protein/L | 12.7 |
| 3.0 mg protein/L | 17.7 |
| 4.5 mg protein/L | 21.5 |
| Detergent + 43kD endoglucanase | |
| 0.3 mg protein/L | 20.3 |
| 0.25 mg protein/L | 18.5 |

Discussion of the results:

The above data clearly demonstrate the criticality of the claimed parameter for the cellulases of the invention over the commercially available Celluzyme.

EXAMPLE II

The following base compositions were prepared:

| | COMPOSITIONS: (all levels in % by weight) | |
|---|---|---|
| | Compact Detergent | Non-compact Detergent |
| LAS | 9.40 | 6.27 |
| TAS | 3.00 | 2.00 |
| FA45E7 | 2.65 | 1.77 |
| Na citrate/citric acid | 18.50 | 12.33 |
| Zeolite 4A | 32.65 | 21.77 |
| Copolymer AA/MA | 4.90 | 3.27 |
| Phosphonate | 0.19 | 0.13 |
| Na carbonate | 3.00 | 2.00 |

We claim:

1. A granular detergent composition comprising surface-active agent, builder and cellulase wherein said cellulase consists essentially of a homogeneous endoglucanase component which is immunoreactive with a monoclonal antibody raised against a partially purified about 43 kD cellulase derived from *Humicola insolens*, DSM 1800;

said granular detergent composition comprising no more than about 15% by weight of inorganic filler salt, and said granular detergent composition having a density of about 550 to about 950 g/liter of composition.

2. A detergent composition according to claim 1 wherein the endoglucanase component of said cellulase has an isoelectric point of about 5.1.

3. A detergent composition according to claim 1, wherein said endoglucanase component is produced by a method comprising cultivating a host cell transformed with a recombinant DNA vector carrying a DNA sequence encoding said endoglucanase component or a precursor of said endoglucanase component as well as DNA sequences encoding functions permitting the expression of the DNA sequence encoding the endoglucanase component, or a precursor thereof, in a culture medium under conditions permitting the expression of the endoglucanase component or precursor thereof and recovering the endoglucanase component from the culture.

4. A detergent composition according to claim 2 wherein said endoglucanase component is produced by a method comprising cultivating a host cell transformed with a recombinant DNA vector carrying a DNA sequence encoding said endoglucanase component or a precursor of said endoglucanase component as well as DNA sequences encoding functions permitting the expression of the DNA sequence encoding the endoglucanase component, or a precursor thereof, in a culture medium under conditions permitting the expression of the endoglucanase component or precursor thereof and recovering the endoglucanase component from the culture.

5. A detergent composition in accordance with claim 1, 2, 3, or 4 wherein the level of the cellulase is such that the amount of enzyme protein to be delivered in the wash solution is from 0.005 to 40 mg/liter of wash solution.

6. A detergent composition according to claim 1 wherein said inorganic filler salt is selected from alkali and alkaline-earth metal salts of sulphate and chloride.

7. A detergent composition in accordance with claim 1 which does not contain more than 10% by wt of inorganic filler salt.

8. A detergent composition in accordance with claim 5 which does not contain more than 10% by wt of inorganic filler salt.

9. A detergent composition in accordance with claim 1 which does not contain more than 5% by wt of inorganic filler salt.

10. A detergent composition according to claim 1 which has a density of 650 to 850 g/liter.

11. A detergent composition according to claim 1, 2, 3 or 4 which is substantially free of phosphate compounds, and wherein said builder is selected from the group consisting of aluminosilicate ion exchangers, citrates, carbonates and mixtures thereof.

12. A granular detergent composition comprising surface-active agent, builder and cellulase wherein said cellulase is an endoglucanase enzyme having the amino acid sequence shown in the appended sequence listing ID#2;

said granular detergent composition comprising no more than about 15% by weight of inorganic filler salt, and said granular detergent composition having a density of about 550 to about 950 g/liter of composition.

13. A detergent composition according to claim 12 wherein said endoglucanase enzyme is produced by a species of Humicola, e.g. *Humicola insolens.*

14. A granular detergent composition comprising surface-active agent, builder and cellulase wherein said cellulase is an endoglucanase enzyme having the amino acid sequence shown in the appended sequence listing ID#4;

said granular detergent composition comprising no more than about 15% by weight of inorganic filler salt, and said granular detergent composition having a density of about 550 to about 950 liter of composition.

15. A detergent composition according to claim 14 wherein said endoglucanase enzyme is produced by a species of Fusarium.

16. A detergent composition according to claim 1, 2, 3 or 4 wherein said enzyme is produced by a DNA construct comprising a DNA sequence encoding the enzyme.

17. A detergent composition according to claim 15 wherein the DNA sequence is as shown in the appended sequence listings ID #1 or ID #3.

18. A detergent composition according to claim 3 or 4 wherein said host cell is a strain of the fungus such as Tricloderuca or Aspergillus, or a yeast cell belonging to a strain of Hansenula or Saccharamyces, e.g. a strain of *Saccharomyces cerevisae.*

19. A detergent composition according to claim 3 or 4 wherein said host cell is a strain of a bacterium, e.g. Bacillus, Streptomyces or *E. coli.*

20. A process for washing fabrics in a washing machine wherein an amount of from 15 to 170 g of a detergent composition according to claim 1 is used for the main wash cycle.

21. A process for washing fabrics according to claim 20 wherein said amount of detergent composition is put in a container able to release the composition at the start of the wash cycle, and said container is placed in the drum of the washing machine, together with the fabrics to be washed.

* * * * *

UNITED STATES PATENT AND TRADEMARK OFFICE
CERTIFICATE OF CORRECTION

PATENT NO. : 5,520,838

DATED : May 28, 1996

INVENTOR(S) : Andre C. Baeck et al.

It is certified that error appears in the above-identified patent and that said Letters Patent is hereby corrected as shown below:

Column 1, line 14 "cellulase-is" should read --cellulase is--.

Column 3, line 4 "oppositions" should read --compositions--.

Column 3, line 10 "no" should read --not--.

Column 5, line 5 "hardhess/g" should read --hardness--.

Column 6, line 3 delete duplicate "and".

Column 6, line 33 "expected used" should read --expected in use--.

Column 11, line 23 "mofidications" should read --modifications--.

Column 12, line 11 "wich" should read --which--.

Column 14, line 20 "mofidiers" should read --modifiers--.

Column 16, line 30 "so s" should read --so as--.

Column 16, line 62 "products" should read --product--.

Column 17, line 26 "Phosphonate: sodium salt of" should be moved to line 27

Column 17, line 33 "Silicate (R=n): SiO2/" should be moved to line 34

Column 18, line 46 Example II is incomplete; please insert before Sequence Listing:

COMPOSITIONS:

( all levels in % by weight )

|  | Compact Detergent | Non-compact Detergent |
|---|---|---|
| Silicate ( R = 2 ) | 2.90 | 1.93 |
| Protease | 1.62 | 1.08 |

UNITED STATES PATENT AND TRADEMARK OFFICE
CERTIFICATE OF CORRECTION

PATENT NO. : 5,520,838

DATED : May 28, 1996

INVENTOR(S) : Andre C. Baeck et al.

It is certified that error appears in the above-identified patent and that said Letters Patent is hereby corrected as shown below:

| | | |
|---|---|---|
| Sulfate | 4.50 | 30.00 |
| SSS | 0.40 | 0.27 |
| Minors + water | balance to 100% | |
| Density : g/L at 20°C) | 680 | 415 |
| Recommended product usage ( g/wash ) | 120 | 180 |

Color Rejuvenation Testing

Test conditions :

Launderometer equipment

Washing temperature : 40°C

Washing time : 3h

Number of wash cycles : 2 pH - 8.2 non-compact detergent
     8.5 compact detergent

Water hardness : 15gr./US gal.

Detergent concentration :
     0.75% for non-compact detergent
     0.66% for compact detergent Test fabric : worn blue pyjama cotton
     (90/10 cotton/Polyester)

UNITED STATES PATENT AND TRADEMARK OFFICE
CERTIFICATE OF CORRECTION

PATENT NO. : 5,520,838
DATED : May 28, 1996
INVENTOR(S) : Andre C. Baeck et al.

It is certified that error appears in the above-identified patent and that said Letters Patent is hereby corrected as shown below:

```
Cellulases : 1) Celluzyme^R supplied by Novo Nordisk
                (= reference)
             2) 43kD endoglucanase = cellulase
                according to the present invention
```

Wash test : Swatches of 8g of worn blue pyjama fabric were treated with the different wash solutions. After tumble drying, the fabrics were graded for colour clarification effects by direct comparison of the two different detergent matrices at equal cellulase level. Visual grading by expert judges using a 0 to 4 scale was preferred. (0 stands for no difference and 4 stands for very big difference.)

Test Results :

I) <u>Non-Compact Detergent</u>

|  | PSU | mg protein/PSU |
|---|---|---|
| NO cellulase | 0 | |
| Celluzyme | | |
| 138 mg protein/L | + 2.3 | 60 |
| 43kD endoglucanase | | |
| 18.6 mg protein/L | + 2.2 | 8.5 |

UNITED STATES PATENT AND TRADEMARK OFFICE
CERTIFICATE OF CORRECTION

PATENT NO. : 5,520,838

DATED : May 28, 1996

INVENTOR(S) : Andre C. Baeck et al.

It is certified that error appears in the above-identified patent and that said Letters Patent is hereby corrected as shown below:

II) Compact Detergent

|  | PSU | mg protein/PSU |
|---|---|---|
| NO cellulase | 0 |  |
| Celluzyme |  |  |
| 165 mg protein/L | + 3.8 | 43 |
| 43kD endoglucanase |  |  |
| 3.4 mg protein/ | + 3.4 | 1.0 |

LSD (Least Significant Difference) = 0.5 PSU

From the mg protein/PSU result, the following efficiency factors were calculated :

Efficiency factor of 43kD endoglucanase versus Celluzyme :

in Non Compact Detergent          in Compact Detergent

60/8.5 = 7                                              43/1.0 = 43

Efficiency factor in Compact Detergent versus in Non Compact Detergent of Celluzyme                                       of 43kD endoglucanase

60/43 = 1.4                                           8.5/1 = 8.5

UNITED STATES PATENT AND TRADEMARK OFFICE
CERTIFICATE OF CORRECTION

PATENT NO. : 5,520,838

DATED : May 28, 1996

INVENTOR(S) : Andre C. Baeck et al.

It is certified that error appears in the above-identified patent and that said Letters Patent is hereby corrected as shown below:

Conclusions :

The above results show a cellulase selected according to the present invention is 43 times more effective than a state-of-the-art cellulase in the claimed compact matrix. Furthermore, the above results show that the performance enhancement due to the claimed compact matrix seen with the selected cellulases is surprisingly much higher than what can be obtained with a state-of-the-art cellulase.

EXAMPLE III.
CLAY SOIL REMOVAL TESTING

Cellulase enzymes also are very efficient in removing clay stains from fabrics. This particular performance characteristic has been checked for a 43kD endoglucanase in the two detergent compositions given in example II.

Conditions:

Linitest equipment
60C wash ( heat up cycle )
Wash time: 40 min.
Water hardness: Brussels city water
Detergent concentrations:
  0.66% for the Compact detergent
  1.0% for the non compact detergent

UNITED STATES PATENT AND TRADEMARK OFFICE
CERTIFICATE OF CORRECTION

PATENT NO. : 5,520,838

DATED : May 28, 1996

INVENTOR(S) : Andre C. Baeck et al.

It is certified that error appears in the above-identified patent and that said Letters Patent is hereby corrected as shown below:

Cellulase concentrations: 1.55, 3.10, 4.65 and 6.2mg enzyme protein / L wash liquor.

Wash test:

Muslin cotton fabric was soiled with naturally-derived clays of two different locations (US, UK). Cellulase performance was evaluated by comparing the clay stains washed at equal cellulase level in the two different detergent compositions. The visual grading scale used in example II was again preferred.

Results:

| Cellulase level: | 1.55 | 3.1 | 4.7 | 6.2 |
|---|---|---|---|---|
| ( mg enz. prot. / L wash liquor ) | | | | |
| Compact detergent | | | | |
| US clay | + 1.50 | + 2.50 | + 2.00 | + 1.50 |
| UK clay | + 0.50 | + 1.00 | + 1.50 | + 2.50 |
| Non compact detergent (=reference) | 0 | 0 | 0 | 0 |

LSD ( least significant difference ) = 0.42 at 95% confidence.

UNITED STATES PATENT AND TRADEMARK OFFICE
CERTIFICATE OF CORRECTION

PATENT NO. : 5,520,838

DATED : May 28, 1996

INVENTOR(S) : Andre C. Baeck et al.

It is certified that error appears in the above-identified patent and that said Letters Patent is hereby corrected as shown below:

The clay stain removal performance of the cellulase selected according to the present invention, in the compact detergent composition of the invention is significantly superior to the performance of the same cellulase in the conventional, non compact detergent composition.

EXAMPLES IV-XI

The following compact detergent compositions are also prepared :

COMPACT DETERGENT COMPOSITIONS:
( all levels in % by weight )

| EXAMPLE | IV | V | VI | VII | VIII | IX | X | XI | XII |
|---|---|---|---|---|---|---|---|---|---|
| LAS | 9.40 | 12.50 | 11.00 | — | 7.58 | 7.58 | 8.20 | 6.50 | — |
| TAS | 3.00 | — | — | — | 2.43 | 2.43 | 2.65 | 3.25 | 3.90 |
| AS | — | — | 4.80 | 12.00 | — | — | — | — | — |
| FA45E7 | 2.65 | 2.00 | 4.00 | 1.00 | 5.11 | 5.11 | 3.15 | 2.20 | 6.00 |
| CAT | — | — | — | — | — | — | — | — | 2.45 |
| Coconut glucose amide | — | 11.00 | — | — | — | — | — | — | — |
| Tallow glucose amide | — | — | — | 10.00 | — | — | — | — | — |
| Na citrate/citric acid | 20.50 | 29.50 | 18.00 | 18.00 | — | 5.00 | 23.50 | 12.00 | 15.00 |
| Zeolite 4A | 33.65 | — | 32.00 | 32.50 | 23.80 | 15.65 | — | 16.00 | 20.00 |
| SKS-6 | — | — | — | — | — | 12.50 | — | — | — |
| Copolymer AA/MA | 4.90 | — | 4.10 | 5.00 | 5.60 | 2.90 | 3.50 | 3.45 | 3.45 |
| PAA | — | 5.70 | — | — | — | — | 1.50 | — | — |
| Phosphonate | 0.19 | 0.23 | 0.19 | 1.00 | 0.57 | 0.43 | 0.30 | — | — |
| EDTA | — | — | — | — | 0.25 | — | — | 0.32 | 0.32 |
| Na carbonate / bicarbonate | 2.00 | 12.00 | 3.28 | 2.50 | 17.30 | 8.00 | 2.50 | 9.90 | 9.90 |
| Silicate ( R = 2 ) | 3.00 | 4.20 | 3.00 | 2.00 | 2.00 | 2.50 | 2.30 | 2.50 | 2.50 |
| CMC | — | 0.15 | — | — | 0.48 | 0.34 | 0.25 | — | — |
| Clay | — | — | — | — | — | — | 12.00 | 8.60 | 8.60 |

UNITED STATES PATENT AND TRADEMARK OFFICE
CERTIFICATE OF CORRECTION

Page 8 of 9

PATENT NO.   : 5,520,838
DATED        : May 28, 1996
INVENTOR(S)  : Andre C. Baeck et al.

It is certified that error appears in the above-indentified patent and that said Letters Patent is hereby corrected as shown below:

| | | | | | | | | | |
|---|---|---|---|---|---|---|---|---|---|
| PB1 | — | — | — | — | 13.12 | 13.12 | 11.47 | 11.50 | — |
| PB4 | — | — | — | — | — | — | 3.55 | — | — |
| Percarbonate | — | — | — | — | — | — | — | — | 12.00 |
| TAED | — | — | — | — | 5.70 | 5.70 | 2.47 | 3.20 | — |
| NOBS | — | — | — | — | — | — | 2.00 | — | — |
| P A. | — | — | — | — | 0.002 | 0.002 | — | 0.003 | 0.003 |
| Protease | 1.62 | 1.30 | 1.20 | 1.60 | 1.35 | 1.35 | 1.05 | 1.40 | 1.40 |
| Lipolase | — | — | 0.40 | 0.30 | — | 0.20 | — | 0.30 | 0.30 |
| Amylase | 0.15 | — | 0.20 | 0.30 | — | 0.10 | — | — | — |
| Sulfate | 2.54 | 3.79 | 2.38 | 2.45 | 1.50 | 1.50 | 2.23 | 3.45 | 3.45 |
| Brightener | — | 0.27 | 0.27 | 0.27 | 0.24 | 0.24 | 0.24 | 0.24 | 0.24 |
| SSS | 0.40 | 0.40 | 0.40 | 0.40 | 0.65 | 0.65 | 0.50 | 0.50 | 0.50 |
| Minors + water | | | | | balance to 100% | | | | |
| Cellulase | at levels so as to deliver $0.01 < X < 10$ mg enzyme protein / wash liquor | | | | | | | | |

UNITED STATES PATENT AND TRADEMARK OFFICE
CERTIFICATE OF CORRECTION

PATENT NO. : 5,520,838
DATED : May 28, 1996
INVENTOR(S) : Andre C. Baeck, et al.

It is certified that error appears in the above-indentified patent and that said Letters Patent is hereby corrected as shown below:

Column 30, line 2 "950 liter" should be --950g/litre--.
Column 30, lines 16 and 17, delete ", e.g. a strain of *Saccharomyces cerevisae*"

Signed and Sealed this

Third Day of December, 1996

Attest:

BRUCE LEHMAN

*Attesting Officer*          *Commissioner of Patents and Trademarks*